United States Patent
Merkus

(10) Patent No.: US 9,737,526 B2
(45) Date of Patent: Aug. 22, 2017

(54) METHODS FOR TREATING PARKINSON'S DISEASE

(71) Applicant: INNOTESTO BVBA, Kasterlee (BE)

(72) Inventor: Franciscus Wilhelmus Henricus Maria Merkus, Kasterlee (BE)

(73) Assignee: INNOTESTO BVBA, Kasterlee (BE)

( * ) Notice: Subject to any disclaimer, the term of this patent is extended or adjusted under 35 U.S.C. 154(b) by 0 days.

(21) Appl. No.: 15/344,758

(22) Filed: Nov. 7, 2016

(65) Prior Publication Data

US 2017/0112822 A1 Apr. 27, 2017

Related U.S. Application Data

(63) Continuation of application No. 14/431,634, filed as application No. PCT/EP2013/070243 on Sep. 27, 2013, now abandoned.

(30) Foreign Application Priority Data

Sep. 28, 2012 (GB) .................................. 1217419.9

(51) Int. Cl.
*A61K 31/407* (2006.01)
*A61K 31/473* (2006.01)
*A61K 9/08* (2006.01)
*A61K 9/00* (2006.01)
*A61K 47/10* (2017.01)
*A61K 45/06* (2006.01)

(52) U.S. Cl.
CPC ............ *A61K 31/473* (2013.01); *A61K 9/006* (2013.01); *A61K 9/08* (2013.01); *A61K 45/06* (2013.01); *A61K 47/10* (2013.01)

(58) Field of Classification Search
USPC ................................... 514/17.7, 210.21, 277
See application file for complete search history.

(56) References Cited

U.S. PATENT DOCUMENTS

2010/0249170 A1 9/2010 Watts et al.
2011/0111011 A1 5/2011 Giovinazzo et al.

FOREIGN PATENT DOCUMENTS

WO WO00/76509 A1 * 12/2000 ............. A61K 31/44
WO WO-00/76509 A1 12/2000

OTHER PUBLICATIONS

International Search Report Issed in PCT/EP2013/070243 on Dec. 12, 2013.

* cited by examiner

*Primary Examiner* — Pancham Bakshi
(74) *Attorney, Agent, or Firm* — Mintz Levin Cohn Ferris Glovsky and Popeo, P.C.; Muriel Liberto, Esq.

(57) ABSTRACT

An oromucosal solution comprising about 1-8% (w/v) apomorphine or a pharmaceutical acceptable salt thereof solubilised in a non-aqueous carrier containing at least about 50% (v/v) of propylene glycol. A small volume (25-250 μL) of said solution containing about 1-12 mg apomorphine may be administered upon demand to treat motor fluctuations during off periods in patients suffering from Parkinson's disease. The solution may also be used for the treatment of sexual dysfunction.

11 Claims, 3 Drawing Sheets

METHODS FOR TREATING PARKINSON'S DISEASE

FIELD OF INVENTION

The present invention relates to oromucosal apomorphine compositions, and has particular reference to a liquid pharmaceutical preparation containing apomorphine that can be used for oromucosal administration for the treatment of patients suffering from Parkinson's disease or other diseases or conditions for which apomorphine is indicated. The invention also provides a method of treating a patient suffering from off-periods in Parkinson's disease or other symptoms of the disease by administering oromucosally the apomorphine preparation of the invention.

BACKGROUND OF THE INVENTION

Apomorphine is prescribed in therapy for a number of indications. As a major indication, apomorphine may be used by injection or infusion to give benefit to patients with Parkinson's disease experiencing 'wearing off' or sudden and unpredictable 'on/off' fluctuations. Also apomorphine is prescribed to alleviate the dyskinesia and akinesia and it is also used effectively to treat sexual dysfunction. The terms 'on/off' or 'motor fluctuations' refer to when a patient finds he/she can no longer rely on the smooth symptom control that their drugs normally give them. Patients deriving the most benefit from apomorphine treatment are those with severe 'off' periods, but who are reasonably well when 'on'.

Apomorphine can be administered in different ways: By a disposable pen to give intermittent injections or as an infusion via a syringe driver using a pre-filled syringe or as ampoules that are used with a continuous infusion pump.

Apomorphine can cause short-term nausea in the beginning of the treatment, and therefore an anti-nausea drug such as domperidone may be given for at least two weeks.

Many attempts have been made to make alternative non-parenteral apomorphine products, such as nasal sprays, nasal powder, and sublingual tablets. From the literature it is clear that attempts to develop a nasal product have failed so far, because of severe side effects in the nose in the form of vestibulitis, leading to a discontinuation of the treatment. Also a number of studies have reported that sublingual administration of apomorphine tablets is effective, but an unpredictable and sometimes long time to benefit may not offer any advantage as a rescue type of therapy. Comparison of 3 mg apomorphine subcutaneous injection and 30 mg apomorphine sublingual tablets in nine Parkinson's disease subjects in a blinded cross-over trial, found that the time to peak benefit was beyond 40 minutes with sublingual apomorphine, as compared with 21 minutes for the subcutaneous preparation. Chronic use of the sublingual formulation was associated with severe stomatitis in half the subjects. Other papers report that the occurrence of stomatitis of sublingual tablets at higher dosages may lead to cessation of treatment (Koller W and Stacy M, Neurology 2004;62:S22-S26).

To avoid the degradation (mainly oxidation) of apomorphine in a liquid composition attempts have been made to separate the apomorphine active agent in one compartment from a second compartment containing a carrier for the drug substance. A recent patent application (US 2009/0023766) describes a study using a two compartment kit consisting of an apomorphine powder compartment and a solvent compartment which are combined just before being squirted onto a volunteer's tongue. The study results are similar to those described in WO 97/06786, which discloses oral fast-dissolving compositions for dopamine agonists, and in WO 99/66916, which describes slow release apomorphine-containing dosage forms for ameliorating male erectile dysfunction. In another recent application (US 2011/0111011) a great variety of sublingual apomorphine containing gels, lozenges, pills, tablets, films or strips are described.

For nasal delivery of apomorphine mainly aqueous solutions of apomorphine have been described in the literature. The aqueous solubility of apomorphine is only about 10 mg/ml (1% w/w). This means that with the usual nasal spray volume of 0.1 ml per nostril, the maximum achievable dose per nostril is too low, about 1 mg apomorphine. Also apomorphine in aqueous nasal sprays is extremely susceptible to oxidation and therefore attempts to develop nasal sprays containing a lot of water have failed so far. An additional problem is nasal irritation and vestibulitis which is most probably caused by the oxidation products of apomorphine.

In WO2005/041966 more concentrated aqueous solutions of apomorphine as dibenzoylester are described for intranasal administration, comprising apomorphine 3.5% w/w. These solutions contain a lot of water in addition to propylene glycol as solvent up to a concentration of 40% (w/w). WO00/76509 discloses a variety of aqueous and non-aqueous apomorphine nasal compositions which may comprise a range of different solvents. Propylene glycol is mentioned as an effective solvent in vitro, however WO00/76509 does not report any in vivo testing of nasal compositions comprising propylene glycol and fails to reveal that propylene glycol in concentrations above 50% is extremely damaging for the nasal mucosa.

WO2005/067893 teaches that propylene glycol, glycerol, polyethylene glycol and povidone are attractive solubilizers for use in nasal products, because in low concentrations they do not have a strong adverse effect on ciliary movement in the nose. Disclosed are in vitro experiments, according to a previously published method (Merkus et al, 2001), describing the effect of four different solubilizers [25% propylene glycol, 15% glycerol, 25% polyethylene glycol 400 and 5% povidone], dissolved in a Locke-Ringer solution, on the ciliary beat frequency (CBF) of ciliated tissue. All four solvents show a strong decrease in CBF after 15 minutes. However, after rinsing with a pure Locke-Ringer solution, the effects on CBF appeared to be completely reversed within 20 minutes.

However, further experiments which have now been carried out using the abovementioned method show that propylene glycol in concentrations of 50% (v/v) are extremely ciliotoxic. The results of these experiments are illustrated in FIGS. 1, 2 and 3, from which it will be seen that after 5-15 minutes contact with 50% propylene glycol all cilia activity is completely arrested. No ciliary beat frequency could be measured any more. Furthermore, rinsing with a Locke-Ringer (LR) solution after 15 minutes did not result in an activation of the ciliated cells. Obviously the ciliated cells have been irreversibly damaged by the extreme hyperosmolar concentration of 50% propylene glycol. The effects of 10% and 25% propylene glycol are reversible, whilst the effect of 50% is not reversible, as demonstrated in FIGS. 1, 2 and 3. Thus, a nasal formulation containing a drug like apomorphine, dissolved in 50% or more (v/v) propylene glycol, is not a viable option, because it has to be administered in Parkinson's disease on a regular basis, for instance daily or several times per day or per week. On the other hand, such a high concentration of propylene glycol is needed to solubilise sufficient apomorphine (several mg per 0.1 ml) to treat a patient with off-periods in Parkinson's disease.

There is a strong medical need for a stable apomorphine formulation which is specifically formulated for treating off-periods in Parkinson's disease, without having the abovementioned disadvantages and problems.

It is an aim of the present invention to provide such a formulation. The formulation of the present invention contains at least about 50% propylene glycol to solubilise a sufficient amount of apomorphine in a small volume to allow adequate doses of apomorphine to be comfortably administered via the buccal and gingival route. A small volume is necessary because otherwise the administered solution is swallowed immediately and apomorphine is not active because it is metabolized in the gastrointestinal tract.

The buccal and gingival mucosa does not contain ciliated cells and has a much more robust structure than the nasal mucosal tissues. The buccal mucosa contains about 40 cell layers while in contrast the nasal ciliated epithelial cells consist of only one cell layer. Also, a nasal puff of 0.1 ml, containing 50% or more propylene glycol, is not only detrimental for the nasal ciliated mucosa, but also extremely irritating in the nose, while such a spray on the buccal mucosa is not irritating, in fact the taste of propylene glycol in the mouth is sweet.

As a consequence, a high concentration of propylene glycol (50% and more) can be used safely on the buccal mucosa, making it possible to solubilise and administer a sufficient amount of apomorphine. The present invention compositions provide a buccal/gingival pharmaceutical formulation of apomorphine causing as little irritation in the mouth as possible and having as high a bioavailability as possible and in a small volume, which is not swallowed easily. This present invention further offers a therapy to treat off periods in Parkinson's patients by providing an apomorphine buccal/gingival solution in the range of for instance 25-100 µl, containing at least 50% (v/v) of propylene glycol as solvent and comprising up to about 8 mg of apomorphine per 100 µl.

SUMMARY OF THE INVENTION

In one aspect of the present invention there is provided an oromucosal solution comprising about 1-8% (w/v) apomorphine or a pharmaceutical acceptable salt thereof solubilised in a non-aqueous carrier containing at least about 50% (v/v) of propylene glycol.

By using the oromucosal solution of the invention, a therapeutically effective dose of about 1-12 mg apomorphine may advantageously be administered to a subject in need thereof in the form of a free liquid having a volume of about 25-250 µL, preferably 25-150 µL. Conveniently the solution may be administered in the form or drops or as a spray or by means of a dosage pen.

Apomorphine and, most probably, its oxidation products are harmful to the mucous membranes in the oral cavity (stomatitis). The oromucosal solution of the present invention offers advantages over prior art formulations because of its extreme small volume and high concentration, both offering rapid and efficient absorption of apomorphine in the oral cavity. It has been found that the greater the concentration of apomorphine in solubilised form, the more efficient is the diffusion of apomorphine through the mucous membranes in the oral cavity. As a consequence, there is less time and less total amount of drug available for degradation to potentially toxic degradation products.

The greater the concentration of the apomorphine in the composition and the smaller the volume, the better the oromucosal absorption of apomorphine. The normal volume of the saliva in the mouth of a human male is about 1.1 mL. A volume of about 0.3 mL, mainly saliva in the sublingual area, is swallowed every minute. This means that an oromucosal spray having a small volume of about 100-150 µL, or less, will remain for a large part in the oral cavity for several minutes, during which time the active agent apomorphine can be absorbed through the oromucosal mucosal membranes. In other words, when the volume of the apomorphine dose administered oromucosally is small, for instance about 100-150 µL or less, the residence time of the major part of the apomorphine in the oral cavity is several minutes, in which time oromucosal absorption takes place.

Under normal circumstances the saliva in the sublingual area of the oral cavity is swallowed first. This means that although the solution of the invention may be administered sublingually or palatally in some embodiments, buccal or gingival application of the apomorphine composition may be particularly advantageous to keep the residence time of the drug and time needed for efficient absorption in the oral cavity as optimal as possible. As a consequence, the volume per dose unit to be administered may be small, for instance less than about 250 µL, suitably less than about 150 µL, and typically about 100 µL or less. Volumes of about 25 µL, about 50 µL, about 100 µL, or volumes between these values, containing doses of about 1-8 mg apomorphine administered to a patient in a single or multiple oromucosal application are suitable to administer the required dosage of apomorphine.

The concentration of apomorphine in the solution is generally in the range of about 1-8% (w/v), but in some embodiments a concentration in the range 1, 1.5 or 2% to 6 or 7% (w/v) may be suitable. For instance a concentration of 3%, 4% or 5% (w/v) may be used.

The use of a non-aqueous solvent is also advantageous because it provides for a more stable product, since the degradation of apomorphine is favoured by an aqueous environment and by oxygen and light.

In accordance with the invention the oromucosal solution of the present invention may be administered to a patient in need thereof. The volume of solution administered should contain at least a therapeutically effective amount of apomorphine for the disease of condition being treated.

Suitably, the oromucosal solution of the invention may be used for the treatment of patients suffering from Parkinson's disease. In particular, the solution of the invention may be used for the treatment of patients suffering from off-periods in Parkinson's disease or as a rescue therapy. It has been found that the solution of the invention may be administered advantageously as an acute treatment when needed to Parkinsonian subjects who are receiving a different chronic medication for treatment of their condition, but are suffering from an acute off-period or the like. Thus the solution of the present invention may be administered upon demand when a patient receiving a different treatment for Parkinson's disease, for example levodopa, experiences motor fluctuations between regular doses of levodopa or another drug. In some cases, the solution of the invention may be administered to patients who suffer from off periods of more than about 30 mins.

Thus, in another aspect of the present invention there is provided a method of treating Parkinson's disease, particularly during off periods, comprising administering oromucosally to a subject in need thereof in the form of a free liquid a dose of about 25-250 μL of a solution comprising about 1-8% (w/v) apomorphine or a pharmaceutically acceptable salt thereof.

The oromucosal solution of the invention may also be used for alleviating dyskinesia or akinesia, for instance in patients with Parkinson's disease, or for treating sexual dysfunction in male or female human subjects.

The volume of the solution administered with each dose may be 25-150 μL or any of the other volumes specified above in relation to use of the solution.

Suitably, about 1-12 mg or about 2-12 mg of apomorphine may be administered at a dosing interval of at least 2 hours, for example at intervals of about 2-12 hours, or about 2-8 hours, in particular at intervals of about 2 hours, about 4 hours or about 8 hours.

In some embodiments, the solution of the invention may be co-administered with an effective amount of an anti-emetic agent (e.g. domperidon).

The present invention offers a new dosage regimen for treating off-periods in Parkinson's disease, which dosage regimen can be described as follows. A non-aqueous solution of apomorphine for use in the treatment of off-periods in patients with Parkinson's disease, wherein the solution is administered oromucosally, in particular buccally and gingivally, in a small volume of 25-150 μl, containing 2-12 mg of apomorphine, at intervals of about 2-8 hours during the day.

In yet another aspect of the present invention there is provided a dosage form containing an amount of the oromucosal solution of the invention, wherein said dosage form is adapted to dispense upon actuation a predetermined volume of about 25-250 μL of said solution as a free liquid containing about 1-12 mg apomorphine.

In some embodiments the dosage form may be adapted to dispense about 25-150 μL of said solution per actuation, or any of the other volumes specified above in connection with the use of the solution of the invention.

The dosage form may suitably comprise a device that is adapted to dispense said predetermined volume in the form of a spray or one or more drops. Said dosage form may comprise a spray device, a drop device, a unit dose device, a multi-dose device or ampoule, a dosage pen or a dosage pipette.

DETAILED DESCRIPTION OF THE INVENTION

Figure 1:
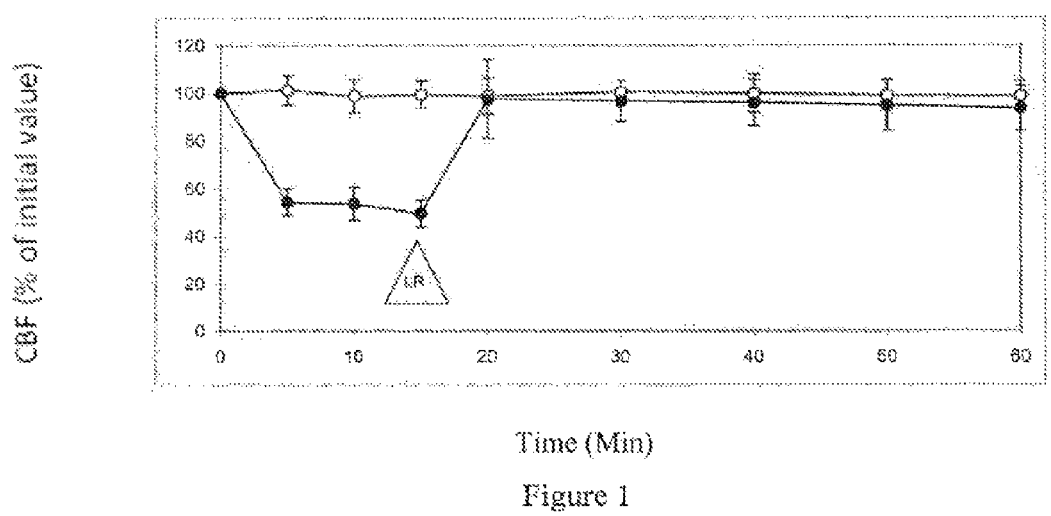
FIG. 1 is a graph showing the effect of 10% (v/v) propylene glycol (closed circles) or control (open circles) on ciliary beat frequency (CBF) of ciliated respiratory tissue. After 15 minutes contact with 10% (v/v) propylene glycol, tissue is rinsed with pure Locke-Ringer (LR) solution.
Figure 2:
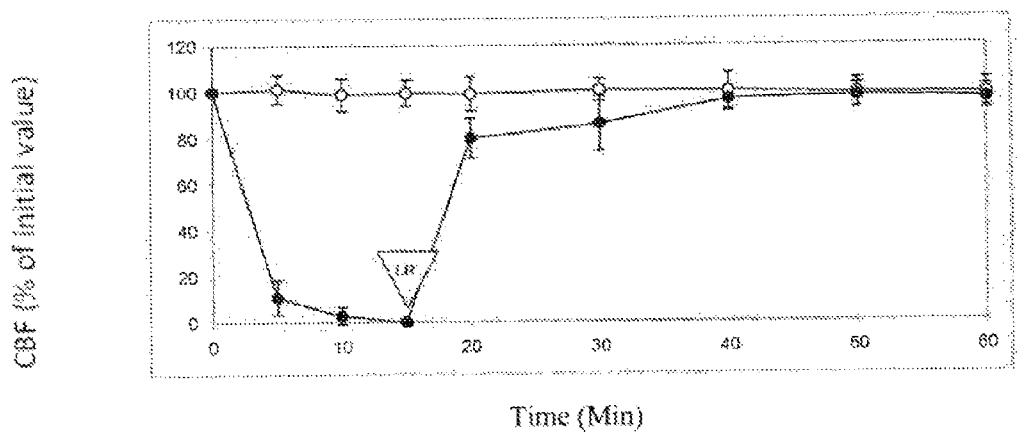
FIG. 2 is a graph showing the effect of 25% (v/v) propylene glycol (closed circles) or control (open circles) on ciliary beat frequency (CBF) of ciliated respiratory tissue. After 15 minutes contact with 25% (v/v) propylene glycol, tissue is rinsed with pure Locke-Ringer (LR) solution.
Figure 3:
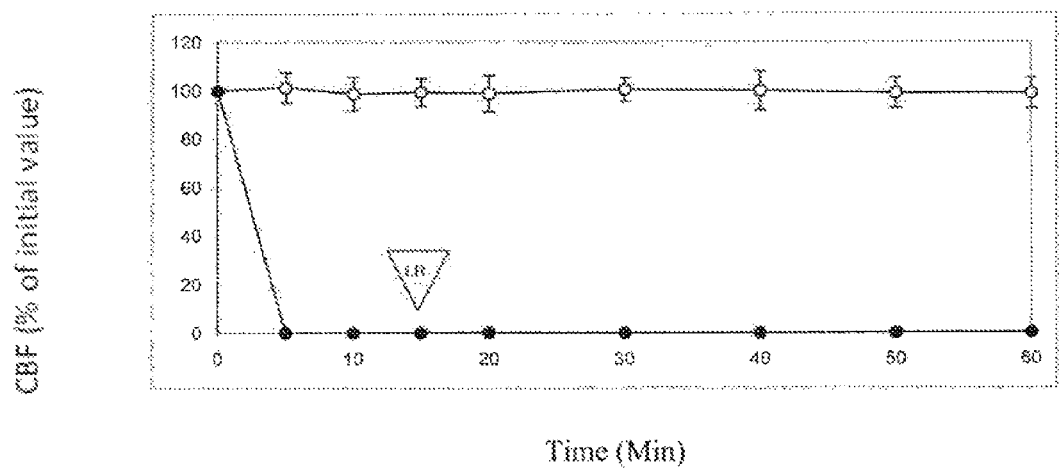
FIG. 3 is a graph showing the effect of 50% (v/v) propylene glycol (closed circles) or control (open circles) on ciliary beat frequency (CBF) of ciliated respiratory tissue. After 15 minutes contact with 50% (v/v) propylene glycol, tissue is rinsed with pure Locke-Ringer (LR) solution.

Oromucosal administration means deposition of the solution of the present invention on the buccal, gingival, palatal or sublingual mucosal epithelium in the oral cavity of a human subject.

In a series of experiments, the solubilities of several constituents that may be used in the solution of the present invention were measured:

| Apomorphine HCl: | Propylene glycol | 80 mg/mL |
|---|---|---|
| | Glycerol | 35 mg/mL |
| | PEG 400 | 15 mg/mL |
| | Ethanol | 20 mg/mL |
| Ascorbic acid: | Propylene glycol | 50 mg/mL |
| | Glycerol | 10 mg/mL |
| | Ethanol | 20 mg/mL |
| Saccharin sodium: | Propylene glycol | 250 mg/mL |
| | Ethanol | 20 mg/mL |

These results show that it is feasible to make an oromucosal composition of apomorphine by solubilising apomorphine in a small volume of propylene glycol—or propylene glycol mixed with other non-aqueous solvents—at a concentration of about 10-80 mg/mL to obtain a solution containing about 1-8 mg apomorphine per 100 μL. In some embodiments a concentration of apomorphine of about 20-70 mg/mL or about 30-50 mg/mL may be employed to obtain a solution containing about 2-7 mg, or about 3-5 mg respectively, of apomorphine per 100 μL.

The results also show that it is possible to add ascorbic acid at a concentration of up to about 50 mg/mL (about 5% w/v). The inclusion of a small amount of an antioxidant such, for example, as ascorbic acid in the solution of the present invention may be desirable in some embodiments to help stabilise the apomorphine against oxidation. Suitably the solution may comprise about 1-10 mg/mL (about 0.1-1% w/v) antioxidant. Other suitable antioxidants are known to those skilled in the art For instance, it has also been found that it is possible to include sodium edetate or sodium metabisulfite in the solution, which are both also known as antioxidants used in pharmaceutical products containing agents (such as apomorphine) that are readily oxidised in solution by oxygen and influence of light.

It has been found that the non-aqueous solution of the invention is more stable than water-containing compositions. In stability experiments using ultraperformance liquid chromatography (UPLC) we confirmed that, in accordance with the scientific literature, apomorphine hydrochloride in aqueous solutions is not stable. It is quickly decomposed on storage. It could be demonstrated that non-aqueous solutions containing apomorphine hydrochloride in propylene glycol were more stable, and the best results were obtained using a very pure propylene glycol (super refined propylene glycol).

The main constituent of the solution is propylene glycol having a concentration of at least 50% (v/v). In some embodiments the propylene glycol may have a concentration of at least 60%, 70%, 80%, 90% or 100% (w/w, w/v or v/v)

Suitably said propylene glycol may have a viscosity of about 30-50 mPa·s measure at 25° C. In some embodiments, the propylene glycol may have a viscosity of about 35-45 mPa·s, e.g. about 40 mPa·s.

The inclusion of about 1-50% (v/v) ethanol in the solution may enhance the absorption of apomorphine in the oral cavity. In some embodiments the solution may comprise about 10-40% (v/v) or about 20-30% (v/v) ethanol. Suitably the solution may comprise about 1-50% (v/v), about 10-40% (v/v) or about 20-30% (v/v/) ethanol, and about 50-99% (v/v), about 60-90% (v/v) or about 70-80% (v/v) propylene glycol. In some embodiments, the carrier may consist of only these two components to which the active agent and other excipients such as antioxidants, flavouring and sweeteners may be added.

Advantageously propylene glycol may be used in the solution of the present invention in the form of a pure or substantially pure solvent. In particular it is desirable that the propylene glycol should be free or substantially free of divalent metal ions (cations). Such a high purity of propylene glycol can be obtained, for example, by pre-treatment with cation exchangers, oxycellulose or cotton wool.

An example of a pure propylene glycol is Super refined Propylene Glycol.

The solution of the invention may contain apomorphine in the form of the hydrochloride salt (water-free or apomorphine HCl.½ H$_2$O). Alternatively the free base form or any other pharmaceutically acceptable salt, ester or prodrug derivative may be used.

In some embodiments the solution of the present invention may comprise a liquid medicament suitable for oromucosal administration comprising from about 10 mg/mL to about 80 mg/mL of apomorphine, apomorphine hydrochloride or any other pharmaceutical acceptable salt of apomorphine in solution in a wholly non-aqueous liquid medium comprising about 50-100% of propylene glycol, substantially free of divalent metal ions, optionally an antioxidant, for instance ascorbic acid, sodium metabisulfite or sodium edetate, and optionally one or more auxiliary solvents selected from ethanol, isopropanol and other polyhydroxysolvents. Said polyhydroxysolvents include glycerol, polyethylene glycol 200-600 and alkoxypolyethylene glycols.

Other auxiliary liquids, known as solvents for pharmaceutical products in the pharmaceutical literature, can also be used in combination with propylene glycol in the compositions of the present invention. Examples are: dimethylsulfoxide (DMSO), dimethyl isosorbide (DMI) and N-methyl-2-pyrrolidone (NMP) and Glycofurol. These ingredients may increase the solubility of apomorphine when they are added to the compositions as presented here in the examples. Also it is possible that these solvents increase or accelerate the absorption through the oromucosal (buccal/gingival) mucosal layers.

Also permeation (penetration) enhancers (e.g. chitosan, bile salts, surfactants, azone, fatty acids) may be included in the compositions for oromucosal use of the present invention.

The taste of the non-aqueous solvent used in the solution will usually be neutralised rapidly by the saliva. However, to mask the bitter taste of apomorphine, one or more sweeteners or flavouring agents may be included. Suitable sweeteners include saccharin, aspartame, cyclamate, xylitol, sucralose, maltitol, sorbitol, erythritol, stevia and other compounds known from the pharmaceutical literature or their salts or derivatives. By way of example, saccharin sodium, saccharin calcium or saccharin may be used.

When a mixture of propylene glycol and other solvents are used, the overall viscosity should not exceed 200 mPa·s, preferably 100 mPa·s and more preferably 50 mPa·s when measured at about 22-25° C.

Suitably, all of the ingredients and excipients in the solution of the invention should be pure or substantially pure and free or substantially free of divalent cations ions to resist the degradation of apomorphine in the presence of catalysing cations.

The solution of the present invention is suitable for oromucosal administration to human or non-human subjects for the treatment of Parkinson's disease, especially to patients with Parkinson's disease who are experiencing 'wearing off' or sudden and unpredictable 'on/off' fluctuations, and in general to Parkinsonian patients for the purpose of alleviating akinesia or dyskinesia.

Alternatively, the solution of the invention may be used for the treatment of male or female sexual dysfunction.

The oromucosal solution of the invention is advantageously administered in small volume doses that contains about 1-12 mg apomorphine. For instance, each dose of the solution may comprise 25 µL, 50 µL, 75 µL, 100 µL or 150 µL of said solution—or any predetermined intermediate volume between these values. This is advantageous for the reasons mentioned above and means that the solution of the invention provides an effective rescue therapy for Parkinsonian subjects or for the treatment of sexual dysfunction that is easy and convenient to administer upon demand. The subject can self-administer the solution by delivering a small volume spray or drops onto the oromucosal membrane in the mouth, particularly buccally or gingivally. The small volume is so small that it is hardly perceived in the mouth by the subject, if at all, and does not provoke a swallowing reflex, allowing the solution to remain on the membrane for sufficiently long for an effective dose to be administered into the blood stream.

The oromucosal solution of the invention may be administered by means of a unit dosage form capable of delivering a predetermined volume of said solution upon actuation, e.g., 25 µL, 50 µL, 75 µL, 100 µL or 150 µL.

In some embodiments, the dosage form may comprise a device adapted to dispense the predetermined volume of solution as a spray or in one or more drops.

Alternatively, the dosage form may comprise a dosage pen or dosage pipette.

In some embodiments the dosage form may comprise a device for single or multiple administrations. The solution may be administered using a multi-dose dispenser or a unit dose dispenser. The dispenser may have an orifice diameter in the range 0.05-0.1 mm depending on the viscosity of the solution. For instance, if needed, the diameter of the discharge orifice of a unit dose spray device may be increased from about 0.05 mm to 0.07 mm because a solution containing mainly propylene glycol may be rather viscous.

In a further embodiment the dosage pen or pipette may comprise a cartridge containing the apomorphine solution. The cartridge may be replaceable. The cartridge may contain the solution for single or for multiple administrations. The cartridge may contain the apomorphine solution wherein the apomorphine is completely in solution or the cartridge consists of a dual chamber wherein the apomorphine powder in one chamber and the solvent in the other chamber are mixed (reconstitution) before administration of the apomorphine solution to the buccal/gingival mucosa of the patient. Such devices are well known in the art (e.g ypsomed.com; vetter-pharma.com).

Suitably the solution may be administered buccally or gingivally. The dosage form may be fitted with an actuator or a discharge orifice to enable the patient or carer to deposit the dose accurately to the gingival or buccal mucosal epithelium.

In another embodiment the oromucosal solution may be administered with a dosage pen delivering a fixed volume containing a fixed dose of 1-12 mg apomorphine. The dosage pen may be equipped with a dosage dial and provided with numbers indicating the required dose per activation or the total number of dosages given.

To resist oxidation of the apomorphine, the solution may be manufactured under nitrogen or another inert (nonoxidising) gas such as argon. Similarly, the dosage form may be filled under nitrogen or another inert gas.

The solution of the invention may be stored under an inert gas such as nitrogen in the dosage form. In some embodiments the dosage form may be filled with nitrogen or another suitable gas to resist oxidation during the shelf life of the product.

Suitably the solution may also be stored in the dosage form in the dark to avoid the deleterious effects of light on apomorphine.

For the treatment of "off-periods" in Parkinson's disease, a dose of about 25-150 μl of said solution comprising about 1-12 mg of apomorphine may be administered at a dosing interval of at least 2 hours.

By administering one or more sprays (puffs) or one or more drops, or by selecting a specific volume of a dosage pen or dosage pipette, the patient or the carer can easily titrate the required dosage at a particular time or medical condition.

EXAMPLES

All excipients are of extra pure pharmaceutical quality. All solutions are protected from light exposure. Propylene glycol and other solvents used have the highest purity and in any case are completely free of divalent cations or they have been made free of divalent cations after pre-treatment with cation exchangers, oxycellulose or cotton wool.

| Apomorphine HCl | 1, 2, or 3 or 4 or 5 or 6, 7 or 8 g |
| --- | --- |
| Sodium metabisulfite | q.s. |
| Sodium edetate | q.s. |
| Flavouring agent | q.s. |
| Sweetener | q.s. |
| Ethanol | 1-50 mL |
| Propylene glycol up to | 100 mL |

100 μL = 1, 2, 3, 4, 5, 6, 7 or 8 mg apomorphine HCl (q.s. = as needed)

| Apomorphine HCl | 1, 2, or 3 or 4 or 5, 6,7 or 8 g |
| --- | --- |
| Ascorbic Acid | 0.1-1 g |
| Sodium Edetate | 0.1% w/v |
| Saccharin Na | 25 mg |
| Propylene glycol | 100 mL |

100 μL = 1, 2, 3, 4, 5, 6, 7 or 8 mg apomorphine HCl (q.s. = as needed)

Table 1 shows the effect of 10% (v/v) propylene glycol on ciliary beat frequency (CBF) of ciliated respiratory tissue. After 15 minutes contacts with 10% (v/v) propylene glycol, tissue is rinsed with pure Locke-Ringer (LR) solution.

TABLE 1

10% propylene glycol in Locke-Ringer solution

| Time (min) | CBF (% of initial value) | | | | | Mean | SD |
| --- | --- | --- | --- | --- | --- | --- | --- |
| 0 | 100 | 100 | 100 | 100 | 100 | 100 | 0 |
| 5 | 46 | 58 | 56 | 51 | 60 | 54 | 6 |
| 10 | 50 | 55 | 63 | 55 | 45 | 54 | 7 |
| 15 | 57 | 52 | 43 | 51 | 45 | 50 | 6 |
| 20 | 91 | 92 | 118 | 110 | 76 | 98 | 17 |
| 30 | 94 | 87 | 110 | 99 | 93 | 97 | 9 |
| 40 | 84 | 91 | 109 | 102 | 93 | 96 | 10 |
| 50 | 82 | 103 | 106 | 99 | 86 | 95 | 11 |
| 60 | 85 | 94 | 106 | 99 | 84 | 94 | 9 |

Table 2 shows the effect of 25% (v/v) propylene glycol on ciliary beat frequency (CBF) of ciliated respiratory tissue. After 15 minute contacts with 25% (v/v) propylene glycol, tissue is rinsed with pure Locke-Ringer (LR) solution.

TABLE 2

25% propylene glycol in Locke-Ringer solution

| Time (min) | CBF (% of initial value) | | | | | Mean | SD |
| --- | --- | --- | --- | --- | --- | --- | --- |
| 0 | 100 | 100 | 100 | 100 | 100 | 100 | 0 |
| 5 | 10 | 12 | 11 | 0 | 21 | 11 | 7 |
| 10 | 0 | 7 | 0 | 0 | 7 | 3 | 4 |
| 15 | 0 | 0 | 0 | 0 | 0 | 0 | 0 |
| 20 | 86 | 72 | 85 | 69 | 87 | 80 | 9 |
| 30 | 68 | 101 | 83 | 89 | 94 | 86 | 12 |
| 40 | 97 | 103 | 99 | 89 | 94 | 97 | 5 |
| 50 | 100 | 102 | 103 | 91 | 92 | 98 | 5 |
| 60 | 102 | 103 | 94 | 91 | 94 | 97 | 5 |

Table 3 shows the effect of 50% (v/v) propylene glycol on ciliary beat frequency (CBF) of ciliated respiratory tissue. After 15 minute contacts with 50% (v/v) propylene glycol, tissue is rinsed with pure Locke-Ringer (LR) solution.

TABLE 3

50% propylene glycol in Locke-Ringer solution

| Time (min) | CBF (% of initial value) | | | | | Mean | SD |
| --- | --- | --- | --- | --- | --- | --- | --- |
| 0 | 100 | 100 | 100 | 100 | 100 | 100 | 0 |
| 5 | 0 | 0 | 0 | 0 | 0 | 0 | 0 |
| 10 | 0 | 0 | 0 | 0 | 0 | 0 | 0 |
| 15 | 0 | 0 | 0 | 0 | 0 | 0 | 0 |
| 20 | 0 | 0 | 0 | 0 | 0 | 0 | 0 |
| 30 | 0 | 0 | 0 | 0 | 0 | 0 | 0 |
| 40 | 0 | 0 | 0 | 0 | 0 | 0 | 0 |
| 50 | 0 | 0 | 0 | 0 | 0 | 0 | 0 |
| 60 | 0 | 0 | 0 | 0 | 0 | 0 | 0 |

The invention claimed is:

1. A method of treating a human subject in need thereof for Parkinson's disease, the method comprising administering oromucosally to the subject one or more doses of a solution comprising 1-8% (w/v) apomorphine, or a pharmaceutically acceptable salt thereof, solubilized in a non-aqueous carrier containing at least 50% (v/v) propylene glycol, and an antioxidant.

2. The method of claim 1, wherein the treating comprises alleviating dyskinesia or akinesia, treating motor fluctuations, or treating off-periods in the subject.

3. The method of claim 1, wherein the solution is administered by the subject as a rescue therapy when required by the subject.

4. The method of claim 1, wherein the solution is administered to the subject in the form of a spray or drops or by a dosage pen.

5. The method of claim 1, wherein the solution is administered buccally or gingivally.

6. The method of claim 1, wherein the antioxidant is one or more of ascorbic acid, sodium metabisulfite, and sodium edetate.

7. The method of claim 1, wherein the solution is free of divalent cations.

8. The method of claim 1, wherein the solution is co-administered with an anti-emetic agent.

9. The method of claim 1, wherein each dose of the one or more doses is administered to an oromucosal membrane in the form of a free liquid by way of one or more drops, sprays or puffs.

10. The method of claim 9, wherein each dose of the one or more doses comprises a total dose volume of 25-250 μL of the solution.

11. The method of claim 1, wherein the solution is administered using a dosage pen or pipette or a device that dispenses said predetermined volume in the form of a spray or one or more drops.

* * * * *